(12) United States Patent
Stephens et al.

(10) Patent No.: US 12,400,557 B2
(45) Date of Patent: Aug. 26, 2025

(54) PERFORMANCE OPTIMIZATION IMPLEMENTING VIRTUAL ELEMENT PERTURBATION

(71) Applicant: UNITED STATES OF AMERICA AS REPRESENTED BY THE ADMINISTRATOR OF NASA, Washington, DC (US)

(72) Inventors: Chad L. Stephens, Poquoson, VA (US); Alan T. Pope, Poquoson, VA (US)

(73) Assignee: United States of America as represented the Administrator of NASA, Washington, DC (US)

( * ) Notice: Subject to any disclaimer, the term of this patent is extended or adjusted under 35 U.S.C. 154(b) by 1109 days.

(21) Appl. No.: 16/223,767

(22) Filed: Dec. 18, 2018

(65) Prior Publication Data
US 2020/0193857 A1    Jun. 18, 2020

(51) Int. Cl.
*G09B 19/00*  (2006.01)
*A61B 5/00*  (2006.01)
*G06F 3/01*  (2006.01)

(52) U.S. Cl.
CPC .............. *G09B 19/00* (2013.01); *A61B 5/486* (2013.01); *G06F 3/011* (2013.01)

(58) Field of Classification Search
None
See application file for complete search history.

(56) References Cited

U.S. PATENT DOCUMENTS

| | | | |
|---|---|---|---|
| 8,628,333 B2 | 1/2014 | Prinzel, III et al. | |
| 9,498,704 B1 * | 11/2016 | Cohen | A63F 9/183 |
| 2011/0009777 A1 * | 1/2011 | Reichow | A61B 3/032 |
| | | | 600/595 |
| 2018/0096614 A1 * | 4/2018 | Pradeep | G09B 5/02 |

* cited by examiner

*Primary Examiner* — James B Hull
(74) *Attorney, Agent, or Firm* — M. Bruce Harper; Robin W. Edwards; Trenton J. Roche

(57) ABSTRACT

Methods, systems, and apparatuses for providing virtual reality environments that may be modified based on physiological measurements of a user. A user may be provided a virtual reality environment to perform a task, such as putting a ball into a hole or driving a vehicle. The virtual reality environment may comprise all or portions of the user's view and may comprise one or more portions of reality. A physiological state measurement device may receive measurements of a physiological state of the user. A computing device may determine, based on the measurements, a projected physiological state of the user. Based on the difference between the projected physiological state and a target physiological state, the virtual reality environment may be modified to make the task harder or easier.

17 Claims, 4 Drawing Sheets

PERFORMANCE OPTIMIZATION IMPLEMENTING VIRTUAL ELEMENT PERTURBATION

STATEMENT REGARDING FEDERALLY SPONSORED RESEARCH OR DEVELOPMENT

The invention described herein was made by employees of the United States Government and may be manufactured and used by or for the Government of the United States of America for governmental purposes without the payment of any royalties thereon or therefore.

BACKGROUND

The physiological state of an individual can have significant impact on their ability to perform and/or complete tasks. For example, even when a driver is fully engaged in the act of driving, the driver may become worse at driving when angry, sad, or tired. But the physiological state of an individual may be too nuanced or subtle for easy association with task performance and/or completion. For example, an individual may be capable of performing rudimentary tasks (e.g., running) without regard to even extreme physiological impairment; however, the same individual may find it difficult to perform more nuanced tasks (e.g., riding a motorcycle) under even the most minor physiological impairment. As another example, an individual may be stressed and not realize that they are stressed, and that stress may adversely influence the individual's decision-making skills (e.g., deciding a play) as well as the individual's ability to perform actions (e.g., taking the steps to make the play).

In many circumstances, individuals performing a task are ill-equipped to self-report and/or diagnose their physiological conditions until such conditions become easily detectable. Individuals are often unable to self-diagnose physiological conditions until such conditions reach a detectible threshold. For example, a weight lifter may not detect a drop in blood sugar until the weight lifter feels demonstrably weak or tired. As another example, a football player may not recognize that circumstances at home are causing the player light mental stress, which adversely impacts their athletic performance at a big game. While measuring devices (e.g., blood glucose measuring devices) may be used to test physiological conditions more accurately, individuals rarely use such devices until conditions become readily apparent or until advised by another individual.

In no small part due to the difficulty of monitoring and training control of physiological conditions, individuals are rarely taught how to control their physiological state as part of task instruction. For example, driver's education courses usually feature instruction on how to use turn signals and understand traffic signs, but often relegate physiological condition training to basic warnings (e.g., "don't drive when tired"). But such instruction can frequently be insufficient: after all, even if an individual heeds a warning (e.g., "don't ride a motorcycle when stressed"), the individual may not recognize that they are stressed in the first place.

While concerted efforts may be made to train an individual's control and awareness of their physiological condition, such training may be counterproductive. For example, a golfing instructor may tell a student to not allow the student's anger to affect their swing; however, such instruction may in fact make the student angrier. As another example, a dance instructor may incorrectly diagnose a student's inability to perform a particular dance step as relating to mental distraction, when in fact the student is merely physically tired. As such, incorrect diagnoses of physiological conditions may be more detrimental than helpful.

Accordingly, there is an ongoing need for improvements in training individuals to control their physiological state, particularly in the context of task completion. These and other needs are addressed by one or more embodiments disclosed below.

BRIEF SUMMARY

Aspects of the present disclosure comprises methods, systems, and/or apparatuses for providing biofeedback training of an individual (e.g., the user of a virtual reality (VR), augmented reality (AR), and/or mixed reality (MR) (collectively, VR/AR/MR) system) to attain a physiological state optimally consistent with successful performance of a task. To allow the reader an understanding of the innovation, aspects will be described with respect to example AR/AR/MR systems; however, as would be understood by a person of ordinary skill in the art, one or more combinations of VR, AR, and/or MR features or components may be implemented within any specific embodiment. Further, reference to a single component (e.g., AR but not VR) herein is merely for illustrative or simplicity purposes, and, absent an express disavowal of one or more of VR, AR, or MR, it is understood that any or all of them may be implemented within any specific embodiment or derivations thereof.

In accordance with one or more embodiments, a task may be transmitted, such as through one or more electronic devices to an end user device operable by a user. The transmission may cause an automatic display and/or notification to an end user of the end user device of the task, information regarding the task or the task itself. In some embodiments, an individual may be provided, using a VR/AR/MR computing device, a VR/AR/MR version of the task, such that, for example, virtual elements are overlaid in a display visible to the individual. As such, one or more portions of a display may be real, whereas one or more portions of the display may be virtual. The VR/AR/MR version of the task may be modified based on the physiological state of the individual, as determined by the VR/AR/MR computing device and/or one or more computing devices communicatively coupled to the VR/AR/MR computing device. Based on a difference between a target physiological value and a projected and/or actual physiological value of the individual, the VR/AR/MR version of the task may become more or less helpful to completion of the task. In one or more embodiments, one or more elements, components, or a difficulty or duration of a component or element of the task may be dynamically adjusted based on the difference between the target physiological value and the projected and/or actual physiological value. For example, a golfing game in virtual reality may become easier based on determining that a golfing student's stress levels are increasing beyond an optimal range. Difficulty may be adjusted, for example, by dynamically adjusting one or more parameters of the task (e.g., elements, components, duration, and difficulty, amongst others). As another example, a target shooting game may become more difficult based on determining that a game player's stress levels exceed a target level. As such, the individual's probability of successfully completing the task may be made proportional (or inversely proportional) to the difference between the target physiological value and the actual physiological value.

As an example of such a VR/AR/MR system, the task may entail putting a golf ball into a hole on a putting green, and the physiological condition may be the anger of the golfer. As such, the goal may be for the golfer to be capable of controlling a mental state (e.g., one or more properties may be utilized to estimate "anger" or "frustration", which may be the same or different properties weighted in different ratios in different implementations). The determinations may be made while instructing or requesting (e.g., via an electronic system) that a user consistently putt the golf ball into the hole. The golfer may be provided a VR/AR/MR version of the putting green, such as a virtual golf ball and virtual putter with a corresponding virtual projected trajectory line (a "sight line") connecting a virtual hole and the virtual golf ball. All or portions of the VR/AR/MR version of the putting green may be real: for example, the golfer may hold a real golf club that includes one or more sensors, e.g., accelerometers, such that a computing device may track the golfer's swing. A computing device may measure a mental state or change in mental states or level of the golfer. As an example, the computing device may detect the cortisol levels of the golfer using blood testing devices, and then determine a projected stress or anger level based on the cortisol levels. The computing device may determine a difference by comparing the projected stress or anger level of the golfer to the target stress or anger level of the golfer. By way of example, the actual cortisol levels of the golfer may be 50 µg/dl, whereas the target cortisol levels of the golfer may be 10 µg/dl, suggesting an absolute difference value of 40 µg/dl. Based on the difference, the computing device may cause the VR/AR/MR system to modify the VR/AR/MR version of the putting green. For example, in response to determining that the difference value is high, a computing device may cause the putting green to undulate, the projected sight line may become fuzzier, or the like, in turn making the putting task more difficult. The computing device may monitor the golfer to detect improvements in the physiological state, and may cause a corresponding change in the VR/AR/MR version of the task as a result. For example, in response to determining that the golfer's cortisol levels have dropped to 20 µg/dl, the computing device may determine a new difference value of 10 µg/dl, and may cause the VR/AR/MR system to make the task easier by, for example, making the putting green appear to stay still or by making the sight line sharper or more reliable.

As another example, a driving student may be instructed to control their level of distraction during a timed driving task. The student may sit in a car environment (e.g., a driving simulator) which provides a VR/AR/MR driving environment. The student may be challenged to complete, using a virtual vehicle, a circuit on a virtual driving course in under a specific time. A computing device may monitor the distraction of the student to real (e.g., their cell phone) and/or virtual (e.g., virtual billboards) distractions. For example, a level of distraction may be calculated, for example, by monitoring, using an eye tracking device, a quantity of time that the student is keeping their eyes on the road. Based on a difference calculated by comparing the student's actual distraction level with a target distraction level, the virtual vehicle may become slower or faster, a virtual road may become more or less winding, and/or the level of traffic may increase or decrease to adjust difficulty of the task. Improvements in the actual distraction level may be detected by a computing device, which may cause the VR/AR/MR system to provide a faster vehicle, straighter roads, and/or less traffic. Conversely, the computing device may detect that the student has become more distracted, and may in turn cause the VR/AR/MR system to provide a slower vehicle, more difficult roads, and/or more traffic.

These and other features, advantages, and objects of the present disclosure will be further understood and appreciated by those skilled in the art by reference to the following specification, claims, and appended drawings.

DETAILED DESCRIPTION

Figure 1:
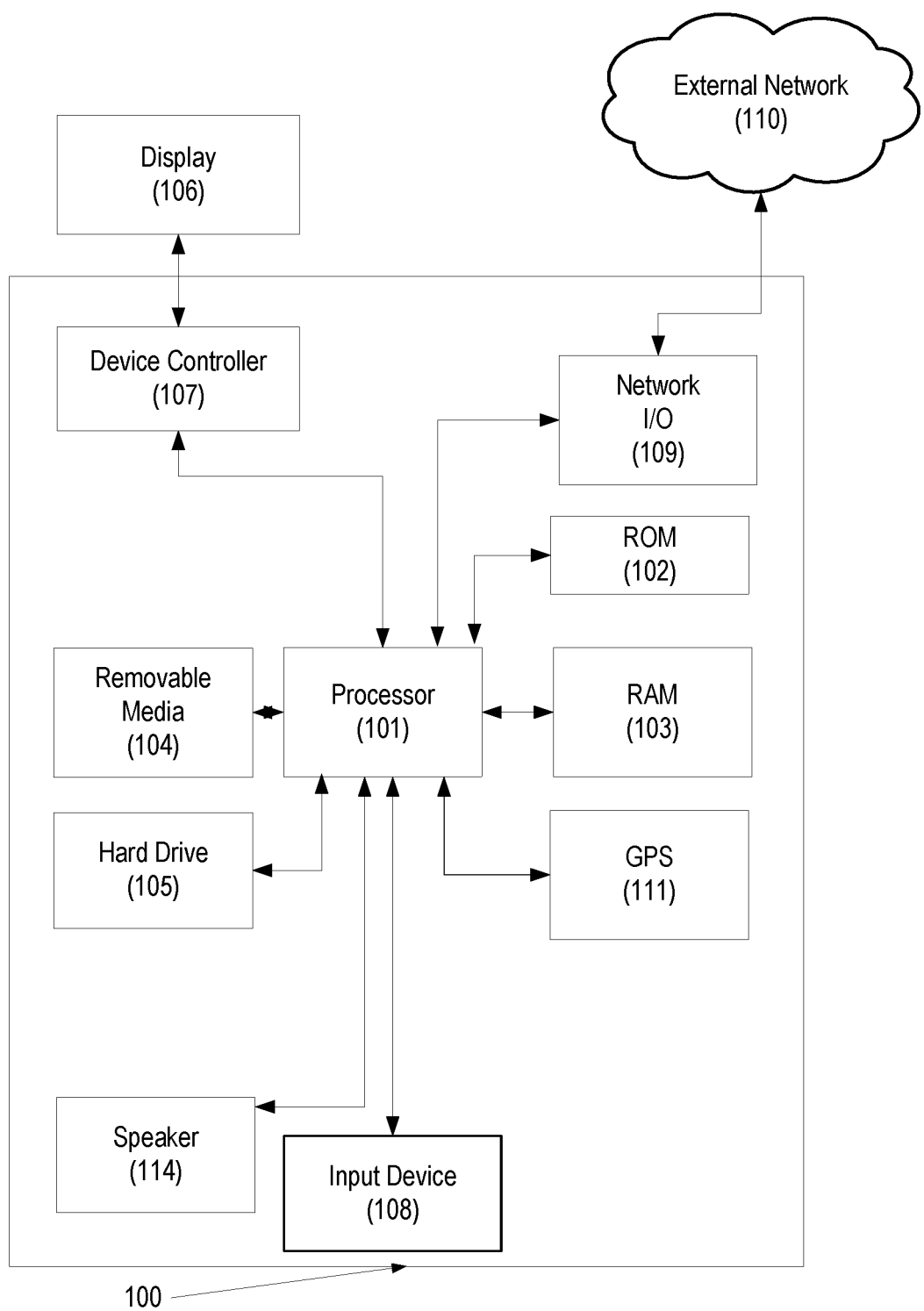
FIG. 1 shows example general hardware elements that can be used to implement a computing devices, consistent with one or more embodiments of the present disclosure.

For purposes of description herein, the terms "upper," "lower," "right," "left," "rear," "front," "vertical," "horizontal," and derivatives thereof shall relate to the embodiment as oriented in FIG. 1. However, it is to be understood that one or more embodiments may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

FIG. 1 shows hardware elements of an example computing device that may be used to implement any of the computing devices discussed herein. Components of FIG. 1 may be used to implement a computing device that may be used to connect to and communicate with one or more other computing devices, e.g., via a network. Such computing devices may include all or portions of, for example, VR/AR/MR devices (e.g., virtual reality headsets, augmented reality glasses), servers, and the like. The computing device 100 may include one or more processors 101, which may execute instructions of a computer program to perform any of the functions described herein. The instructions may be stored in a read-only memory (ROM) 102, random access memory (RAM) 103, removable media 104 (e.g., a Universal Serial Bus (USB) drive, a compact disk (CD), a digital versatile disk (DVD)), and/or in any other type of computer-readable medium or memory. Instructions may also be stored in an attached (or internal) hard drive 105 or other types of storage media. The computing device 100 may include one or more output devices, such as a speaker 114, a display 106 (e.g., an external television or other display device), and may include one or more output device controllers 107, such as a video processor. There may also be one or more input devices 108. The input devices 108 may include, for example, keyboards, mice, motion sensing devices, accelerometers, touchpads, or the like. The computing device 100 may also include one or more network interfaces, such as a network input/output circuit 109 (e.g., a network card) to communicate with an external network 110. The network input/output circuit 109 may be a wired interface, wireless interface, or a combination of the two. The network input/output circuit 109 may include a modem (e.g., a cable modem), and the external network 110 may include, for example, an in-home network, a network provider's wireless, coaxial, fiber, or hybrid fiber/coaxial distribution system (e.g., a Data Over Cable Service Interface Specification (DOCSIS) network), or any other network. Additionally, the device may include a location-detecting device, such as a global positioning system (GPS) microprocessor 111, which may be configured to receive and process global positioning signals and determine, with possible assistance from an external server and antenna, a geographic position of the device.

Although FIG. 1 shows an example hardware configuration, one or more of the elements of the computing device 100 may be implemented as software or a combination of hardware and software. Modifications may be made to add, remove, combine, divide, etc. components of the computing device 100. Additionally, the elements shown in FIG. 1 may be implemented using basic computing devices and components that have been configured to perform operations such as are described herein. For example, a memory of the computing device 100 may store computer-executable instructions that, when executed by the processor 101 and/or one or more other processors of the computing device 100, cause the computing device 100 to perform one, some, or all of the operations described herein. Such memory and processor(s) may also or alternatively be implemented through one or more Integrated Circuits (ICs). An IC may be, for example, a microprocessor that accesses programming instructions or other data stored in a ROM and/or hardwired into the IC. For example, an IC may include an Application Specific Integrated Circuit (ASIC) having gates and/or other logic dedicated to the calculations and other operations described herein. An IC may perform some operations based on execution of programming instructions read from ROM or RAM, with other operations hardwired into gates or other logic. Further, an IC may be configured to output image data to a display buffer.

Figure 2:
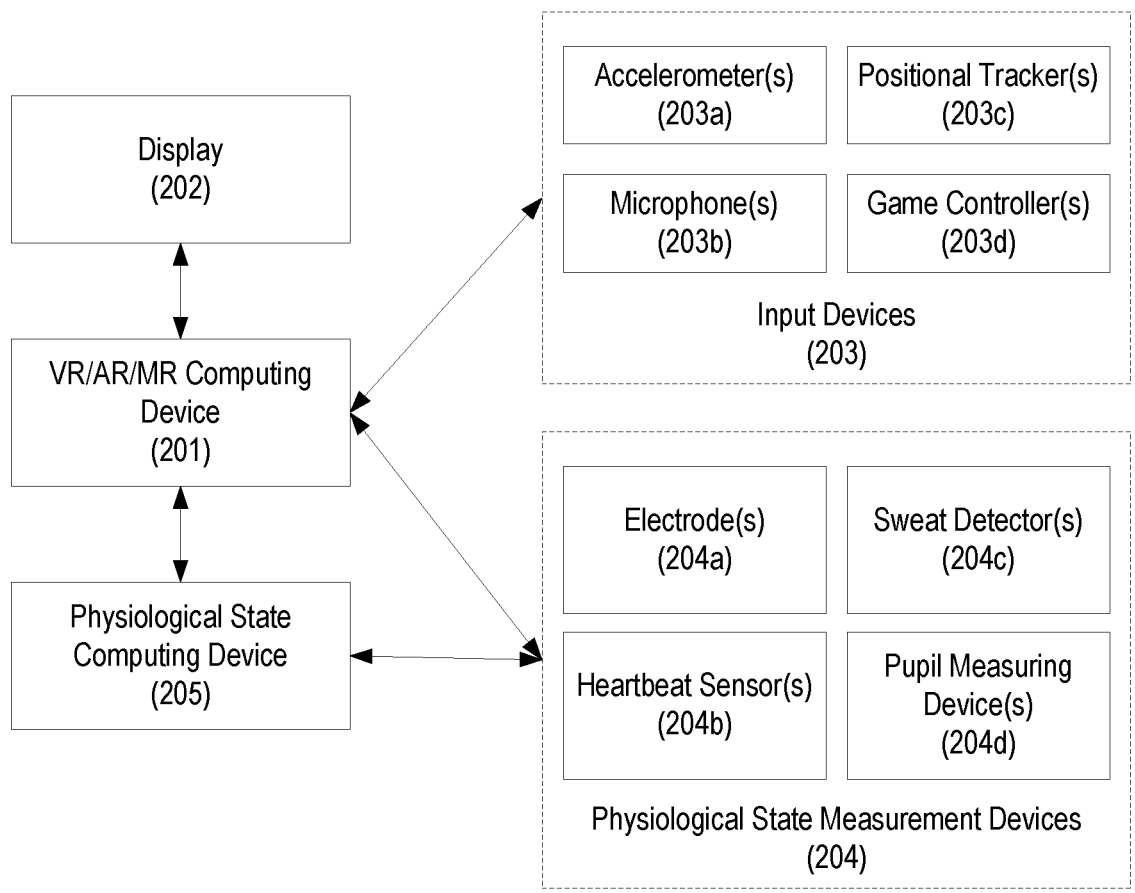
FIG. 2 shows an example VR/AR/MR system comprising a physiological state measurement device, consistent with one or more embodiments of the present disclosure.

FIG. 2 shows an example VR/AR/MR system comprising a physiological state measurement device. The VR/AR/MR system may include a VR/AR/MR computing device 201 communicatively coupled to a display 202 and one or more input devices 203, which may include, for example, accelerometers 203a, microphones 203b, positional trackers 203c, and/or game controllers 203d. The VR/AR/MR system may be communicatively coupled to one or more physiological state measurement devices 204, which may be associated with a physiological state computing device 205. The physiological state measurement devices may include, for example, electrodes 204a, heartbeat sensors 204b, sweat detectors 204c, and/or pupil measuring devices 204d. Either or both the VR/AR/MR computing device 201 and the physiological state computing device 205 may be all or portions of the computing device 100. Similarly, all or portions of the input devices 203 or the physiological state measurement devices 204 may be all or portions of the computing device 100. For example, the accelerometers 203a may comprise processors (e.g., processor 101) for motion processing. Though depicted as separate in FIG. 2, the VR/AR/MR computing device 201 and the physiological state computing device 205 may be executed on the same or similar computing devices (e.g., the same personal computer). Though depicted as separate in FIG. 2, the one or more input devices 203 may be the same as one or more of the physiological state measurement devices 204 (e.g., the positional trackers 203c may also include a heartbeat sensor, or an accelerometer of the accelerometers 203a may be used both for virtual reality input as well as to determine a physiological state of a user).

The VR/AR/MR computing device 201 may be configured to provide, e.g., via the display 202, a VR/AR/MR environment for one or more users. Virtual reality may refer to the provision of an entire virtual environment, e.g., a room with objects within it, in complete replacement of reality. Augmented reality and/or mixed reality may refer to application of virtual objects and/or elements in a real environment. For example, a virtual reality environment may occupy some or all of a user's field of view such that the virtual reality environment replaces reality, whereas an augmented reality environment and/or mixed reality environment may add to, but need not entirely replace, reality. As such, the VR/AR/MR computing device 201 may provide at least one virtual object within an individual's field of view, but need not entirely replace their field of view with an entirely virtual environment unless desired (e.g., to immerse an individual in a virtual environment). Nonetheless, as used herein, the terms "virtual reality," "augmented reality," and "mixed reality" may be interchangeable: for example, a virtual reality environment need not entirely replace all of a user's field of view.

A display, such as display 202, may be any display configured to display content. The display 202 may be the same or similar as the display 106. In a virtual reality context, the display 202 may be a virtual reality display configured to occupy some or all of a user's field of view. For example, the display 202 may be one or more liquid crystal display (LCD) screens with corresponding lenses (e.g., Fresnel lenses) configured to display the screen in some or all of an individual's field of view. In a mixed reality or augmented reality context, the display 202 may be a virtual reality display configured to occupy less than all of a user's field of view. For example, the display 202 may be entirely or partially transparent (e.g., glass configured to refract light in a manner that causes text or an image to appear on top of objects in an individual's field of view). As another example, the display 202 may occupy some or all of a user's view, but may display portions of the real environment surrounding a user via a camera. The display need not be affixed to an individual. For example, the display may be a projector and screen such that a wall is portrayed with virtual elements.

One or more input devices, such as devices 203, may be any devices configured to receive input corresponding to one or more users of the VR/AR/MR system. The input devices 203 may additionally or alternatively include, without limitation, devices configured to detect and/or measure motion (e.g., accelerometers), pressure (e.g., pressure sensors on floor pads), location (e.g., global positioning system devices), sound (e.g., microphones), heat (e.g., temperature sensors), digital input (e.g., game controllers or keyboards), or the like. As shown in FIG. 2, the input devices 203 may include the accelerometers 203a, the microphones 203b, the positional trackers 203c, and/or the game controllers 203d.

Physiological state measurement devices, such as devices 204, may be one or more devices configured to measure one or more physiological states of one or more users of the VR/AR/MR system. As used herein, physiological state may include either or both physical or mental conditions of an individual, or combinations thereof. For example, a physiological state measurement device of the physiological state measurement devices 204 may be configured to determine an individual's tiredness based on their quantity of movement (e.g., how forcefully a player throws a virtual ball) and an individual's level of stress based on their quality of movement (e.g., whether the player's hands shake). The physiological state measurement devices 204 may be the same or similar devices as the input devices 203 and may be configured to detect and/or measure motion, pressure, location, sound, heat, digital input, or the like. As shown in FIG. 2, the physiological state measurement devices 204 may include, for example, the electrodes 204a, the heartbeat sensors 204b, the sweat detectors 204c, and the pupil measuring devices 204d.

The physiological state measurement devices 204 may be configured to measure one or more physical conditions of an individual. The VR/AR/MR computing device 201 and/or the physiological state computing device 205 may be configured to derive physical information through one or more measurements taken via the physiological state measurement devices 204. The physiological state computing device 205 may, for example, be configured to measure exertion of one or more muscles using electrodes (e.g., the electrodes 204a) to determine a projected level of tiredness for all or a portion of the body. The physiological state computing device 205 may additionally or alternatively derive physical information about an individual via, for example, an amount of sweat on the skin (e.g., via the sweat detectors 204c), blood measurements, monitoring of brain activity, heartbeat (e.g., via heartbeat sensors 204b), eye movement (e.g., duration of focus on one or more particular objects depicted by the display 202) and/or pupil dilation (e.g., via pupil measuring devices 204d), or the like.

The physiological state measurement devices 204 may additionally or alternatively be configured to measure one or more mental conditions of the individual. The VR/AR/MR computing device 201 and/or the physiological state computing device 205 may be configured to derive mental information through one or more measurements received via the physiological state measurement devices 204. For example, the movement of a user's eyes (as determined by, for example, a camera pointed at the user's eyes) may suggest the individual's engagement in a task or a level of distraction. As another example, a user's propensity to fidget and/or grind their teeth (as determined by, for example, one or more accelerometers, including those used for input such as the accelerometers 203a) may suggest the user's level of anger or irritation. As yet another example, a user's breathing pattern (as determined by, for example, a microphone) may suggest that the user is tired and/or sleepy.

The input devices 203 and the physiological state measurement devices 204 may be the same or part of similar devices. For example, an accelerometer used for virtual reality input may be additionally used to determine the user's propensity to fidget, suggesting a level of distraction. As another example, voice input provided via a microphone (e.g., microphones 203b) may be analyzed by the physiological state computing device 205 to monitor the clarity and tenor of a user's voice, which may suggest their mental state.

The physiological state computing device 205 may be configured to receive measurements from the physiological state measurement devices 204. The physiological state computing device 205 may be configured to receive and analyze measurements from the physiological state measurement devices 204 and, based on the analysis, transmit projected physiological information to the VR/AR/MR computing device 201. Such projected physiological information may also comprise an estimate of past or future physiological condition(s). For example, in some implementations the physiological state computing device 205 may be configured to receive measurements from the physiological state measurement devices 204 on a periodic basis (e.g., every second), store the measurements received, analyze the stored measurements, and transmit analysis information (e.g., a projected current or future physiological state of a user) to the VR/AR/MR computing device 201.

The physiological state computing device 205 may receive and use additional data to determine physiological information corresponding to the user of the VR/AR/MR system. For example, a test administrator may provide the physiological state computing device 205 information corresponding to the user (e.g., that the user just completed a marathon), which may be used by the physiological state computing device 205 to determine that the user may be sweating due to tiredness, rather than nervousness. As another example, the physiological state computing device 205 may receive, from another computing device such as a temperature measurement computing device, an indication that a building is unusually warm, and the physiological state computing device 205 may on that basis determine that the user is sweating due to being excessively warm, rather than tired and/or stressed.

Figure 3:
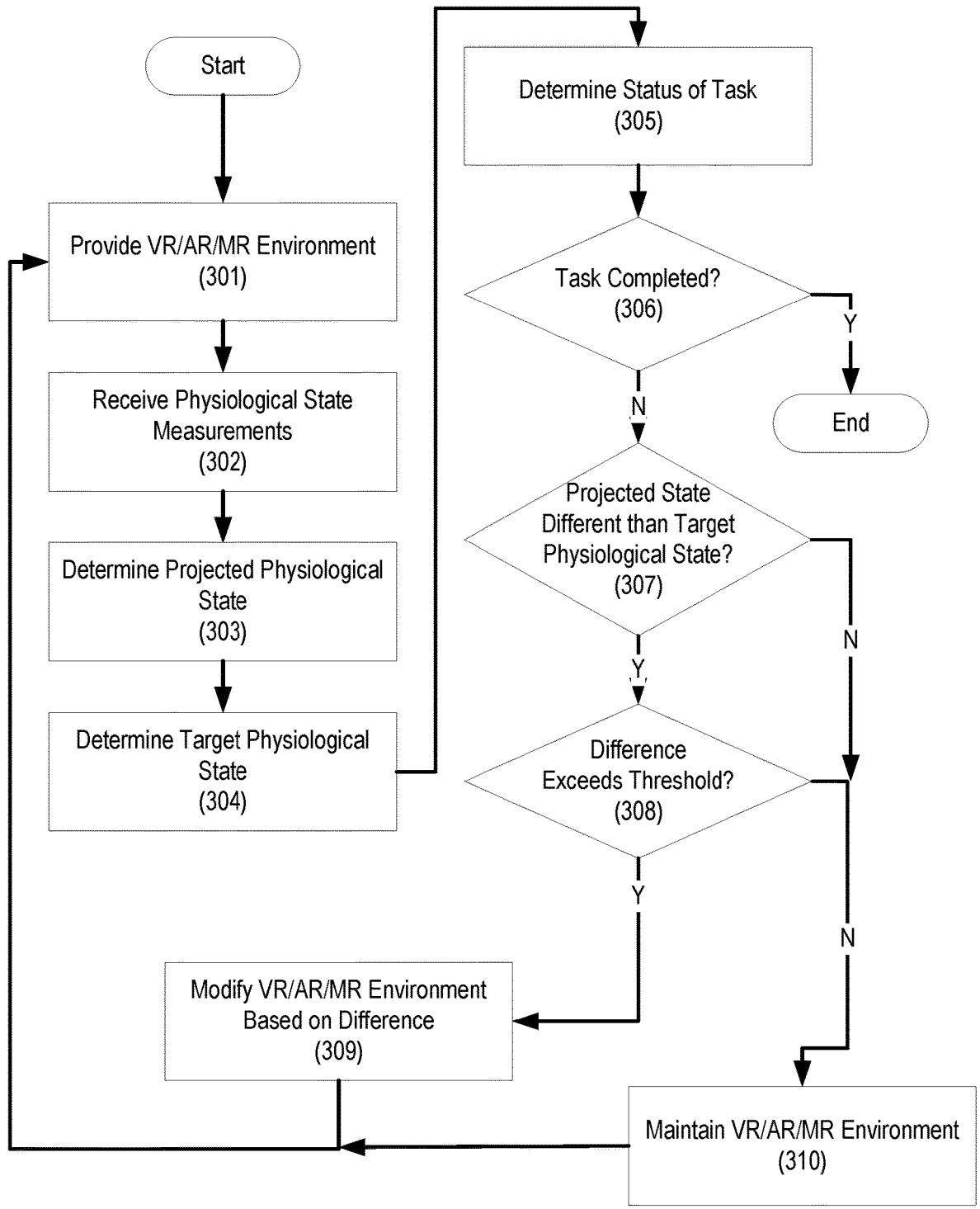
FIG. 3 is a flow chart depicting one or more possible implementations which may be taken by one or more VR/AR/MR systems, consistent with one or more embodiments of the present disclosure.

FIG. 3 is a flow chart depicting steps which may be taken by the VR/AR/MR system. In step 301, the system provides a VR/AR/MR environment. Providing a VR/AR/MR environment may comprise displaying one or more objects, e.g., via the display 202, to a user of the VR/AR/MR system. For example, the user and the VR/AR/MR system may be physically located in the user's bedroom, but the VR/AR/MR system may cause display via, e.g., the display 202, of a rainforest in a remote location. As another example, the VR/AR/MR system may be physically located at a golf course, and the display 202 may show a sight line extending from a golfer's ball to a hole. The user may be capable of interacting with the VR/AR/MR environment using the input devices 203. For example, the user may be able to walk around the virtual environment and interact with one or more objects.

The VR/AR/MR environment may be associated with a task. A task may be any action taken by the user in the real and/or VR/AR/MR environment. Providing the VR/AR/MR environment may comprise prompting the user to perform the task, and monitoring completion of the task. For example, the user may be asked to complete a puzzle using both objects from reality and those depicted in the VR/AR/MR environment, e.g., via display 202. As another example, the user may be required to perform an athletic activity, such as shooting a basketball into a hoop. The task may require feedback from one or more external devices, such as a device configured to determine if a user successfully putted a ball into a hole.

In step 302, the VR/AR/MR system may receive, from the physiological state measurement devices 204, one or more measurements of the physiological state of a user of the VR/AR/MR system. The measurements may be received on a periodic basis, e.g., every ten seconds. Additionally or alternatively, the VR/AR/MR computing device 201 and/or the physiological state computing device 205 may request measurements. The measurements may be received in any manner based on the configuration of one or more physiological state measurement devices 204. For example, the sweat detectors 204c may provide a percentage value every ten seconds (e.g., where 100% indicates that the user is pouring sweat), whereas the pupil measuring devices 204d may provide an exact measurement of the user's pupil dilation when queried (e.g., by the physiological state computing device 205 and/or the VR/AR/MR computing device 201).

At block 303, the VR/AR/MR system may, based on the measurements, determine a projected physiological state of the user. The projected physiological state may be any qualitative or quantitative assessment of the physiological state of a user. For example, the projected physiological state may be a binary condition (e.g., whether or not the user appears tired), a percentage (e.g., a percentage of how stressed the user seems to be), a plurality of subjective assessments (e.g., happy, excited, energetic), or the like.

At block 304, the VR/AR/MR system may determine a target physiological state for the user. The target physiological state may be a result (e.g., that the user becomes happy), a particular value and/or a predetermined threshold (e.g., that the user's eyes remain fixed on a particular object more than 80% of the time), a range (e.g., that the user's cortisol levels remain within a range for a period of time), or the like. The target physiological state may be determined based on the physiological state measurements devices 204 that are available. For example, the VR/AR/MR system may be configured to determine stress level of a user and, if a blood measuring device is not available to determine the cortisol levels of the user, then the VR/AR/MR system may instead use the amount of fidgeting a user does as an indicator of their stress level.

At block 305, the status of the task is determined. The task may be completed, in progress, or have not yet begun. For example, if the task involves putting a ball into a hole, the status of the task may be that the user has not yet putted the ball, that the ball is currently in travel, or that the putting task is complete and the ball is in (or out) of the hole. Determining the status of the task may comprise retrieving information corresponding to the task from one or more computing devices. Additionally or alternatively, determining the status of the task may comprise receiving an indication that the task has been completed, e.g., from an administrator of the task.

In decision 306, the VR/AR/MR system may determine, based on the status of the task, whether or not the task has been completed. If the task has been completed, the flow chart ends. Otherwise, the flow chart continues to decision 307.

In decision 307, the VR/AR/MR system may determine a difference between the projected physiological state of the user and the target physiological state. The difference may be qualitative (e.g., that the user is currently angry and not happy) or quantitative (e.g., that the absolute value of the difference between a target cortisol level and the user's current cortisol level exceeds a predetermined threshold). The difference may be multi-dimensional, e.g., a series of differences of different physiological state measurements and target physiological states. The difference may be an absolute value or may indicate whether the projected physiological state of the user is above or below the target physiological state. If the difference exists, the flow chart proceeds to decision 308. Otherwise, the flow chart proceeds to step 310.

In step 308, the VR/AR/MR system determines whether the difference exceeds a predetermined threshold. Variance and inaccuracies in physiological state measurement devices may exist. For example, a user's cortisol levels may naturally fluctuate around an average. To account for such variance and inaccuracies, the target physiological state may be a range, and/or the projected physiological state may be an average (e.g., of past measurements). For example, the target physiological state may be 10 μg/dl with a predetermined threshold of +/−5%, such that a cortisol level of 10.4 μg/dl would be considered to not exceed the predetermined threshold, whereas a measurement of 9.4 μg/dl would exceed the predetermined threshold. The predetermined threshold may require exactitude, such that the projected physiological state be exactly the same as the target physiological state. If the difference exceeds the predetermined threshold or if no predetermined threshold exists, the flow chart continues to step 309. Otherwise, the flow chart continues to step 310.

The predetermined threshold may be based on the accuracy and reliability of the physiological state measurement devices 204. Some physiological state measurement devices 204 may provide accurate measurements, but such measurements may be of constantly changing values, such that a degree of variance in measurements is to be expected. Similarly, some physiological state measurement devices 204 may be unreliable, such that measurements may vary over time without change in the measured subject. As such, the predetermined threshold may be based on an expected variance of measurements from the physiological state measurement devices 204.

The predetermined threshold may additionally or alternatively be based on the particularities of the measured subject. For example, some individuals may be more prone to sweating than others, or some individuals may be comparatively more difficult to measure using the physiological state measurement devices 204. The threshold may be accordingly modified to account for such variance.

The predetermined threshold may additionally or alternatively be based on the task performed. For example, a meditation task may require that an individual remain as still as possible, and thus the threshold for movement for the meditation task may be less forgiving than a second threshold for a golfing task. As another example, a subject's heart rate may be less important (and a corresponding threshold more forgiving) for a jigsaw puzzle task than for an athletic task.

In block 309, the VR/AR/MR system may modify the VR/AR/MR environment based on the difference between the target physiological state of the user and the projected physiological state of the user. Modification of the VR/AR/MR environment may entail modification of one or more parameters affecting the task. For example, if the task is putting a golf ball into a hole, modification of the task may entail blurring a sight line connecting a hole and the golf ball, such that successful putting becomes more difficult. As another example, if the task is a puzzle, two related pieces of the puzzle may be highlighted such that completing a portion of the puzzle becomes easier. After step 309, the flow chart may return to step 301.

Modification of the VR/AR/MR environment may be designed to make a task easier. For example, the VR/AR/MR environment may be configured to teach a user to putt a golf ball into a hole without becoming frustrated. Based on determining that the user is more frustrated than a target frustration level, the VR/AR/MR system may provide additional putting guides in the VR/AR/MR environment in order to make the putting task easier. As another example, based on determining that the user is tired, the VR/AR/MR system may provide easier putting opportunities which the user may find more fun and less exhausting.

Modification of the VR/AR/MR environment may be designed to make a task harder. Returning to the putting example above, based on determining that the user is less frustrated than a target frustration level (e.g., that the user has become proficient and bored), the VR/AR/MR system may modify the putting environment to become more difficult (e.g., the green may undulate, the hole may move, part of the green may be hidden). As another example, based on determining that the user has energy and enjoys the putting task, the VR/AR/MR environment may be slowly modified to become progressively more difficult in order to better engage the user.

Modification of the VR/AR/MR environment may be controlled, e.g., via the VR/AR/MR computing device 201, by the user or an administrator. The VR/AR/MR computing device 201 may be configured to perform certain modifications to the VR/AR/MR environment, but not others. For example, the VR/AR/MR computing device 201 may be instructed to not make a puzzle task harder than a certain amount, or to not perform certain modifications to the VR/AR/MR environment (e.g., making objects in the VR/AR/MR environment rapidly move near the user's field of view lest the user become nauseous).

In step 310, if the projected state is not different than the target physiological state (decision 307) and/or if the difference does not exceed the threshold (decision 308), the VR/AR/MR environment is maintained.

Figure 4:
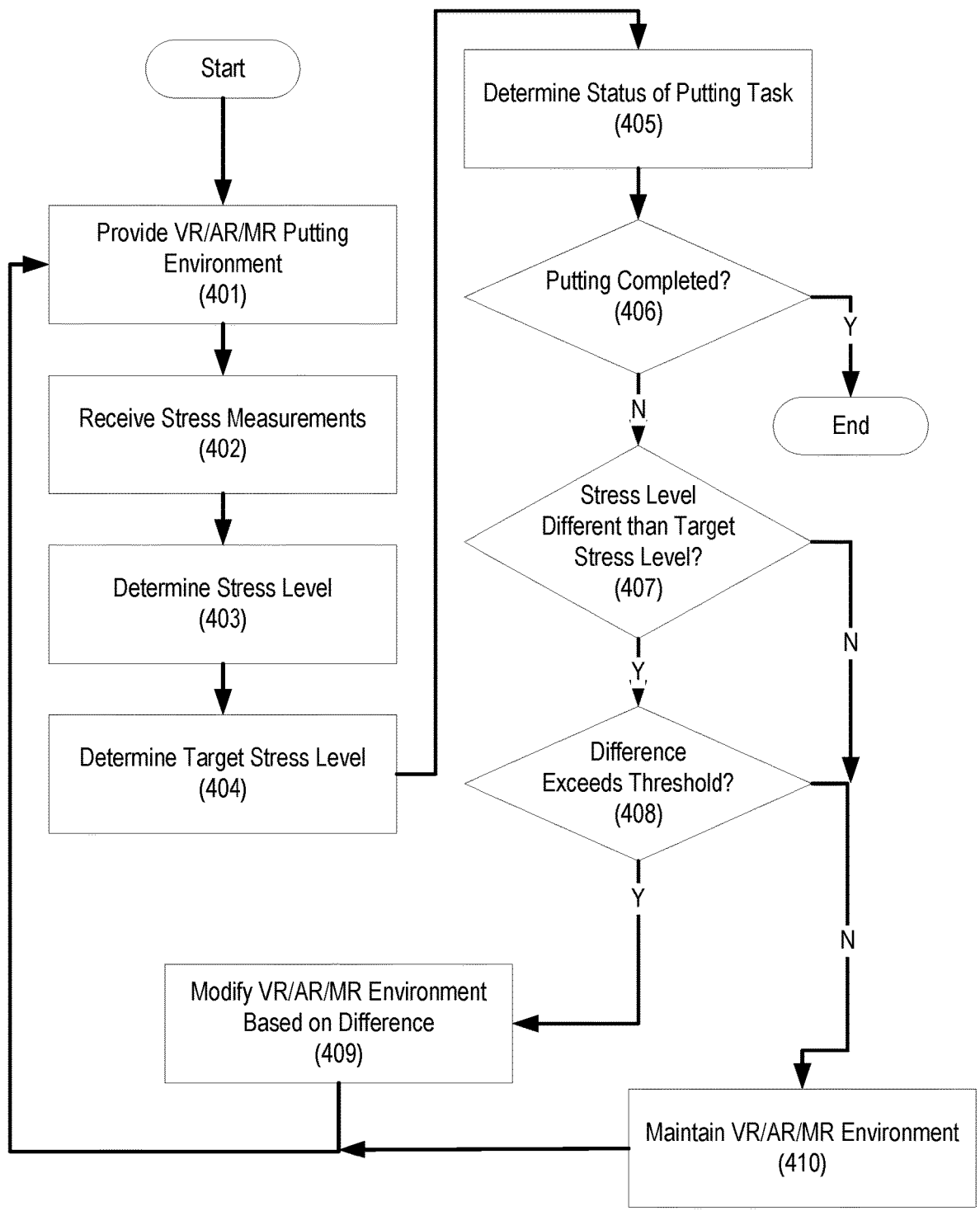
FIG. 4 is a flow chart depicting one or more implementations which may be taken by one or more VR/AR/MR systems in the context of one example putting task.

FIG. 4 is a flow chart example of a VR/AR/MR system designed to help a golfer complete a putting task while maintaining their stress level. In step 401, the VR/AR/MR system may provide the VR/AR/MR putting environment to the golfer. For example, the VR/AR/MR system may render, e.g., on the display 202, a golfing putter, a golf ball, a putting green, and a golf ball on the putting green. The VR/AR/MR system may additionally display information regarding movement of the putter and/or golf ball, such as, responsive to the putter striking the golf ball, velocity, acceleration, timing information, and the like. For example, the VR/AR/MR system may be configured to provide a golfer with information on golf ball speed after the golfer strikes the ball with a putter.

In the VR/AR/MR environment, the user may be prompted to use a combination of both real and virtual elements to putt the golf ball into a hole. For example, the golfer may be shown both a real putter and a real golf ball. Either or both the real putter and/or the real golf ball may be configured with one or more of the input devices 203 and/or one or more of the physiological state measurement devices 204. For example, the golf ball may include one or more of the accelerometers 203*a*, and the handle of the putter may include one or more of the heartbeat sensors 204*b*. On top of the surface of a real putting green, a virtual laser-like sight line and golf hole may be rendered to the golfer via the VR/AR/MR system (e.g., via the display 202). When the golfer hits the ball, the elements of the real environment (e.g., the golf ball) are shown in virtual reality, such that the real putter and golf ball are no longer visible to the golfer. The virtual ball may then move based on the strike.

In step 402, the VR/AR/MR system may receive stress measurements corresponding to the golfer from the physiological state measurement devices 204, such as the electrodes 204*a*. Such measurements may comprise cortisol levels, an amount of fidgeting the golfer is doing, or the like. Different configurations of stress measurement may be implemented depending on the particularities of the golfer. For example, some golfers may express stress verbally (which may entail use of one or more of the microphones 203*b*), whereas other golfers may be more prone to spikes in heart rate (which may entail use of one or more of the heartbeat sensors 204*b*).

In step 403, a stress level may be determined based on the stress measurements from step 402. The stress level may be, for example, expressed as a percentage value, with 100% being the most stressed, and 0% being the least stressed.

In step 404, a target stress level may be determined. The target stress level may depend on the goal of the task in the VR/AR/MR putting environment. For example, the VR/AR/MR system may be configured to intentionally stress the golfer in order to train the golfer to putt better under pressure. As another example, the VR/AR/MR system may be configured to train the golfer to control and lessen stress by rewarding the golfer with more fun putting tasks when the golfer's stress level is at least as low as a target stress level.

At step 405, the status of the putting task is determined by the VR/AR/MR system. For example, as in block 305, the VR/AR/MR system may determine whether or not the user has putted the ball. In decision 406, the VR/AR/MR system may determine, based on the status of the task, whether or not the putting task has completed. If the task has been completed, the flow chart ends. Otherwise, the flow chart continues to decision 407.

In step 407, the VR/AR/MR system may determine a difference between the golfer's stress level and the target stress level. If no such difference exists, the flow chart proceeds to step 410. If the difference does exceed the threshold, the flow chart proceeds to step 408.

In step 408, the VR/AR/MR system may determine whether the difference determined in step 407 exceeds a predetermined threshold. The threshold may, like the target stress level, depend on the particularities of the golfer, the physiological state measurement devices 204, the task, and the like. For example, if the target stress level is a binary condition (e.g., not stressed), then the threshold need not exist. If the difference exceeds the threshold (or if no threshold exists), the flow chart proceeds to step 409. Otherwise, the flow chart continues to step 410.

In step 409, and based on the difference, the VR/AR/MR system may modify the putting environment. The surface of a virtual putting green may be made to undulate with an amplitude based on the difference. A sight line drawn from a putter to a hole may be made to oscillate back and forth with an amplitude based on the difference. The diameter and aperture of a golf hole may be made to increase or decrease based on the difference. One or more portions of the virtual putting green may be obfuscated (e.g., blurred) based on the difference. Animals, such as gophers, may be made to appear and disappear based on the difference, and such animals may be configured to interfere with the putting task (e.g., by stealing the golf ball). One or more virtual explosions may be rendered by the VR/AR/MR system. After step 409, the flow chart may return to step 401.

In step 410, if the stress level is not different than the target stress level (decision 407) and/or if the difference does not exceed the threshold (decision 408), the VR/AR/MR environment is maintained. For example, the VR/AR/MR system may continue to wait for the user to putt the ball.

The VR/AR/MR system described in FIGS. 3 and 4 may be similarly adapted in a driving context to improve driver attention. The VR/AR/MR system may be configured to provide a virtual driving environment. The physiological variable of interest may be a level of distraction when driving, and the physiological state measurement devices 204 may be configured to measure a level of distraction based on, for example, the duration in which a driver's eyes are not focused on the road as measured using a camera. Based on the driver's level of distraction (e.g., the number of times the driver's eyes are not on the road), the VR/AR/MR system may be configured to modify road conditions, e.g., by adding more obstacles, making the virtual road harder to see, or the like. Additionally or alternatively, the VR/AR/MR system may be configured to modify road conditions to be more engaging based on the driver's level of distraction being lower than a threshold. In this manner, the driver may be rewarded by keeping their eyes on the road, and may be punished for distraction.

In one or more embodiments, the VR/AR/MR system described in FIGS. 3 and 4 may be adapted in the context of a flying simulator. The VR/AR/MR system may be configured to provide a virtual plane flying environment (e.g., a flight simulator) where the physiological variable of interest may be a level of tiredness, stress, distraction, boredom, or the like. Based on the physiological state measurements 204, the virtual plane flying environment may be made harder or easier. For example, turbulence may be increased or decreased based on a level of the user's boredom.

In one or more embodiments, the VR/AR/MR system described in FIGS. 3 and 4 may be adapted in the context of medical/surgical procedure simulator. The VR/AR/MR system may be configured to provide a virtual surgical environment, where a user can practice a surgical procedure. The physiological variables of interest during this surgical procedure may be the user's level of distraction, physical exhaustion, or the like. Based on physiological state measurements for the relevant physiological variable(s) of interest, the medical/surgical simulator may be made harder or easier. For example, the patient may become better or increasingly unwell based on the physiological variable of interest in addition to the user's proficiency in performing the procedure. As another example, the VR/AR/MR environment may be more difficult to see based on determining that the user is tired.

Although examples are described above, features and/or steps of those examples may be combined, divided, omitted, rearranged, revised, and/or augmented in any manner. Various alterations, modifications, and improvements will readily occur to those skilled in the art. Such alterations, modifications, and improvements are intended to be part of this description, though not expressly stated herein, and are intended to be within the spirit and scope of the disclosure. Accordingly, the foregoing description is by way of example only, and is not limiting.

What is claimed is:

1. A method of operating a mixed reality (MR) system for training an individual to control one or more physiological conditions during performance of an assigned task in a MR environment, the method comprising:
    displaying, via a display device communicatively coupled to an MR computing device of the MR system, an MR environment containing a virtual reality (VR) portion displaying to the individual a virtual object overlaid in a field of view of the individual using the display device, a physical reality (PR) portion displaying a physical object in the field of view of the individual, and the assigned task for the individual to complete by interacting with a physical object in the PR portion of the MR environment;
    detecting, via a user input device of the MR system, the individual interacting with the physical object;
    determining, via the MR computing device responsive to detecting the individual interacting with the physical object, that the assigned task is incomplete and, if se, responsively:
        determining, based on one or more inputs received from a physiological state measurement device communicatively coupled to the MR computing device, one or more physiological states capable of being measured by the physiological state measurement device;
        selecting, based on the one or more physiological states capable of being measured by the physiological state measurement device, one or more physiological states that impact the individual's ability to successfully complete the assigned task;
        automatically receiving, from the physiological state measurement device communicatively coupled to the MR computing device, one or more measurements of the selected physiological states of the individual, wherein the one or more measurements of the physiological states of the individual comprises at least one of: an amount of sweat on skin, blood measurements, brain activity, heartbeat, eye movement, and pupil dilation;
        automatically receiving, from a physical measurement device communicatively coupled to the MR computing device, one or more measurements of at least one of forces on and movements of the physical object;
        determining, based on the one or more measurements of the selected physiological states, a projected physiological state of the individual;
        determining, based on the one or more measurements of at least one of the forces on and movements of the physical object, a projected trajectory of the physical object;
        modifying a difficulty of the assigned task in proportion to a difference between the projected physiological state and a target physiological state;
        determining, based on modifying the difficulty of the assigned task, one or more modifications to the VR portion within the MR environment; and
        commanding, via the MR computing device while the individual is performing the assigned task, the display device to display a modified VR portion within the MR environment, wherein the one or more modifications to the VR portion within the MR environment comprises updating one or more aspects of the virtual object overlaid in the field of view of the individual in accordance with the modified difficulty of the assigned task, wherein modifying the difficulty of the assigned task comprises increasing a distracting action or reducing the distracting action of the one or more aspects of the virtual object along the projected trajectory of the physical object within the VR portion of the MR environment;
    subsequent to the commanding step, determining, via the MR computing device, if the assigned task is completed; and
    ending, via the MR computing device responsive to determining the assigned task is completed, the training of the individual.

2. The method of claim 1, further comprising: determining a threshold associated with the target physiological state for the individual, wherein modifying the difficulty of the assigned task is further based on determining that the difference meets or crosses the threshold.

3. The method of claim 1, wherein the VR portion of the MR environment rewards the individual for reducing the difference between the projected physiological state and the target physiological state by reducing the distracting action of the one or more aspects of the virtual object along the projected trajectory of the physical object within the VR portion of the MR environment.

4. The method of claim 1, wherein the VR portion of the MR environment punishes the individual for increasing the difference between the projected physiological state and the target physiological state by increasing the distracting action of the one or more aspects of the virtual object along the projected trajectory of the physical object within the VR portion of the MR environment.

5. The method of claim 1, wherein the VR portion of the MR environment occupies a first portion of the field of view of the individual, and the PR portion of the MR environment occupies a second portion, distinct from the first portion, of the field of view of the individual.

6. The method of claim 1, wherein the assigned task is to putt a golf ball into a golf hole.

7. The method of claim 1, wherein the assigned task is to drive a vehicle on a road, hit a golf ball down a fairway, shoot a basketball into a hoop, solve a puzzle, perform a medical or surgical procedure, or pilot an airplane through a flying environment.

8. An apparatus for training an individual to control one or more physiological conditions during performance of an assigned task within a mixed reality (MR) environment, the apparatus comprising:
   one or more processors;
   a physical measurement device communicatively coupled to the one or more MR processors and configured to detect at least one of forces on and movements of physical objects;
   a user input device communicatively coupled to the one or more MR processors and configured to detect movement of the individual;
   a display device communicatively coupled to the one or more MR processors;
   a physiological state measurement device communicatively coupled to the one or more MR processors; and
   a memory device storing instructions that, when executed by the one or more MR processors, cause the apparatus to:
      display, via the display device, an MR environment containing a virtual reality (VR) portion displaying a virtual object overlaid in a field of view of the individual, a physical reality (PR) portion displaying a physical object in the field of view of the individual, and the assigned task for the individual to complete by interacting with a physical object in the PR portion of the MR environment;
      detect, via the user input device, the individual interacting with the physical object;
      determine, responsive to detecting the individual interacting with the physical object, if the assigned task is incomplete and, if so, responsively:
         determine, based on one or more inputs received from a physiological state measurement device communicatively coupled to the MR computing device, one or more physiological states capable of being measured by the physiological state measurement device;
         select, based on the one or more physiological states capable of being measured by the physiological state measurement device, one or more physiological states that impact the individual's ability to successfully complete the assigned task;
         automatically receive, from the physiological state measurement device, one or more measurements of the selected physiological states of the individual, wherein the one or more measurements of the physiological state of the user comprises at least one of: an amount of sweat on skin, blood measurements, brain activity, heartbeat, eye movement, and pupil dilation;
         automatically receive, via the physical measurement device, one or more measurements of at least one of forces on and movements of the physical object;
         determine, based on the one or more measurements of the selected physiological states, a projected physiological state of the individual;
         determine, based on the one or more measurements of the at least one of forces on and movements of the physical object, a projected trajectory of the physical object;
         modify a difficulty of the assigned task in proportion to a difference between the projected physiological state and a target physiological state;
         determine, based on modifying the difficulty of the assigned task, one or more modifications to the VR portion within the MR environment; and
         display, via the display device while the individual is performing the assigned task, a modified VR portion within the MR environment, wherein the one or more modifications to the VR portion within the MR environment comprises updating one or more aspects of the virtual object overlaid in the field of view of the individual in accordance with the modified difficulty of the assigned task, wherein modifying the difficulty of the assigned task comprises increasing a distracting action or reducing the distracting action of the one or more aspects of the virtual object along the projected trajectory of the physical object within the VR portion of the MR environment;
      determine if the assigned task is completed with the individual in control of the one or more physiological conditions at the target physiological state; and
      end training responsive to the assigned task being complete.

9. The apparatus of claim 8, wherein the instructions, when executed by the one or more MR processors, further cause the apparatus to: determine a threshold associated with the target physiological state for the individual, wherein modifying the difficulty of the assigned task is further based on determining that the difference meets or crosses the threshold.

10. The apparatus of claim 8, wherein the VR portion of the MR environment is configured to reward the individual for reducing the difference between the projected physiological state and the target physiological state by reducing the distracting action of the one or more aspects of the virtual object within the VR portion of the MR environment.

11. The apparatus of claim 8, wherein the VR portion of the MR environment is configured to punish the individual for increasing the difference between the projected physiological state and the target physiological state by increasing the distracting action of the one or more aspects of the virtual object within the VR portion of the MR environment.

12. The apparatus of claim 8, wherein the assigned task is to drive a vehicle on a road, hit a golf ball down a fairway, shoot a basketball into a hoop, solve a puzzle, perform a medical or surgical procedure, or pilot an airplane through a flying environment.

13. A system for training an individual to control one or more physiological conditions during performance of an assigned task in a mixed reality (MR) environment, the system comprising:
- an MR display device configured to provide, to the individual, a MR environment; and
- an MR computing device communicatively coupled to the MR display, the MR computing device configured to:
    - display, via the MR display, an MR environment containing a virtual reality (VR) portion displaying a virtual object overlaid in a field of view of the individual, a physical reality (PR) portion displaying a physical object in the field of view of the individual, and the assigned task for the individual to complete by interacting with a physical object in the PR portion of the MR environment;
    - detect, via the user input device, the individual interacting with the physical object;
    - determine, responsive to detecting the individual interacting with the physical object, if the assigned task is incomplete and, if so, responsively:
        - determine, based on one or more inputs received from a physiological state measurement device communicatively coupled to the MR computing device, one or more physiological states capable of being measured by the physiological state measurement device;
        - select, based on the one or more physiological states capable of being measured by the physiological state measurement device, one or more physiological states that impact the individual's ability to successfully complete the assigned task;
        - automatically receive, from the physiological state measurement device, one or more measurements of the selected physiological states of the individual, wherein the one or more measurements of the physiological state of the user comprises at least one of: an amount of sweat on skin, blood measurements, brain activity, heartbeat, eye movement, and pupil dilation;
        - automatically receive, via the physical measurement device, one or more measurements of at least one of forces on and movements of the physical object;
        - determine, based on the one or more measurements of the selected physiological states, a projected physiological state of the individual;
        - determine, based on the one or more measurements of the at least one of forces on and movements of the physical object, a projected trajectory of the physical object;
        - modify a difficulty of the assigned task in proportion to a difference between the projected physiological state and a target physiological state; and
        - determine, based on modifying the difficulty of the assigned task, one or more modifications to the VR portion within the MR environment; and
        - display, via the display device while the individual is performing the assigned task, a modified VR portion within the MR environment, wherein the one or more modifications to the VR portion within the MR environment comprises updating one or more aspects of the virtual object overlaid in the field of view of the individual in accordance with the modified difficulty of the assigned task, wherein modifying the difficulty of the assigned task comprises increasing a distracting action or reducing the distracting action of the one or more aspects of the virtual object along the projected trajectory of the physical object within the VR portion of the MR environment;
    - determine if the assigned task is completed with the individual in control of the one or more physiological conditions at the target physiological state; and
    - end training responsive to the assigned task being complete.

14. The system of claim 13, wherein the MR computing device is further configured to: determine a threshold associated with the target physiological state for the individual, wherein modifying the difficulty of the assigned task is further based on determining that the difference meets or crosses the threshold.

15. The system of claim 13, wherein the VR portion of the MR environment is configured to reward the individual for reducing the difference between the projected physiological state and the target physiological state by reducing the distracting action of the one or more aspects of the virtual object within the VR portion of the MR environment.

16. The system of claim 13, wherein the VR portion of the MR environment is configured to punish the individual for increasing the difference between the projected physiological state and the target physiological state by increasing the distracting action of the one or more aspects of the virtual object within the VR portion of the MR environment.

17. The system of claim 13, wherein the assigned task is to drive a vehicle on a road, hit a golf ball down a fairway, shoot a basketball into a hoop, solve a puzzle, perform a medical or surgical procedure, or pilot an airplane through a flying environment.

* * * * *